United States Patent
Jeong et al.

(10) Patent No.: US 12,421,654 B2
(45) Date of Patent: Sep. 23, 2025

(54) METHOD FOR MANUFACTURING MYCELIUM MAT INTO LEATHER BY USING PH-CONTROLLED TANNIC ACID

(71) Applicant: MYCEL INC., Yongin-si (KR)

(72) Inventors: Yeon Woo Jeong, Seoul (KR); Sung Won Kim, Hwaseong-si (KR)

(73) Assignee: MYCEL INC., Yongin-si (KR)

( * ) Notice: Subject to any disclaimer, the term of this patent is extended or adjusted under 35 U.S.C. 154(b) by 0 days.

(21) Appl. No.: 18/935,678

(22) Filed: Nov. 4, 2024

(65) Prior Publication Data
US 2025/0059703 A1 Feb. 20, 2025

Related U.S. Application Data

(63) Continuation of application No. PCT/KR2022/019190, filed on Nov. 30, 2022.

(30) Foreign Application Priority Data

May 6, 2022 (KR) .................. 10-2022-0056140
Nov. 15, 2022 (KR) .................. 10-2022-0152487

(51) Int. Cl.
| | | |
|---|---|---|
| D06M 13/238 | (2006.01) | |
| D06M 15/03 | (2006.01) | |
| D06M 15/27 | (2006.01) | |
| D06N 3/00 | (2006.01) | |
| D06N 3/14 | (2006.01) | |
| D06M 15/705 | (2006.01) | |
| D06M 101/04 | (2006.01) | |

(52) U.S. Cl.
CPC .......... *D06M 13/238* (2013.01); *D06M 15/03* (2013.01); *D06M 15/27* (2013.01); *D06N 3/0015* (2013.01); *D06N 3/145* (2013.01); *D06M 15/705* (2013.01); *D06M 2101/04* (2013.01); *D06N 3/0077* (2013.01); *D06N 2201/04* (2013.01)

(58) Field of Classification Search
CPC ........................... D06M 13/238; D06M 15/03
See application file for complete search history.

(56) References Cited

U.S. PATENT DOCUMENTS

| | | | | |
|---|---|---|---|---|
| 2020/0399824 | A1* | 12/2020 | Stewart | B01D 11/0203 |
| 2022/0007777 | A1* | 1/2022 | Wang | B32B 7/09 |

FOREIGN PATENT DOCUMENTS

| | | |
|---|---|---|
| JP | 2850003 B2 | 1/1999 |
| JP | 2021052698 A | 4/2021 |
| KR | 20210093294 A | 7/2021 |
| KR | 20220013374 A | 2/2022 |
| KR | 20220024666 A | 3/2022 |
| KR | 20220027075 A | 3/2022 |
| WO | 2021/136883 A1 | 7/2021 |

* cited by examiner

*Primary Examiner* — Cachet I Proctor
(74) *Attorney, Agent, or Firm* — NKL Law; Jae Youn Kim

(57) ABSTRACT

The present invention relates to a method for manufacturing mycelium mat into leather by using pH-controlled tannic acid. The method comprises the following steps: (1) inactivating the mycelium mat; (2) infiltrating the mycelium mat with a polysaccharide solution; (3) treating the polysaccharide-infused mycelium mat with a tannic acid solution; and (4) introducing a buffering agent to the tannic acid-treated mycelium mat. This innovative approach enhances the mechanical properties of the resulting leather, offering an environmentally friendly alternative to conventional leather materials.

6 Claims, 2 Drawing Sheets

METHOD FOR MANUFACTURING MYCELIUM MAT INTO LEATHER BY USING PH-CONTROLLED TANNIC ACID

TECHNICAL FIELD

The present invention relates to a method for manufacturing mycelium mat into leather by using pH-controlled tannic acid, which provides a leather material with improved physical strength, flexibility, and durability. The invention utilizes mycelium, an eco-friendly material that can replace animal leather and petrochemical-based synthetic polymers. More specifically, this invention pertains to a method for producing leather from a mycelium mat using tannic acid with controlled pH levels.

BACKGROUND ART

As global demand and preference for leather continue to increase, there is a corresponding rise in consumer expectations for ethical consumption. Consequently, there is an increasing need for alternative leather materials (synthetic leather) that do not involve large-scale animal slaughter or environmental degradation during the production process.

However, artificial leather differs significantly in texture compared to natural leather, making the molding process more complex to meet consumer expectations. As a result, the processing and molding steps involving dyeing and adhesion have increased, leading to a sharp rise in manufacturing costs. Additionally, since the production of artificial leather relies on petroleum-based polymers that are not easily degradable, the material is not recyclable. This leads to significant environmental pollution throughout the entire manufacturing process, from production to disposal as industrial waste, posing multiple challenges.

Therefore, there is an urgent necessity for the development of a manufacturing method that utilizes a novel material capable of replacing animal leather and conventional synthetic leather. This method must address the environmental and ethical concerns associated with traditional leather production, providing a sustainable and ethical alternative that meets current market demands.

In light of the aforementioned circumstances, extensive research is actively being conducted on the production of leather using materials such as plant fibers, mushrooms, and silicone, which can serve as substitutes for natural animal leather.

However, the physical properties of leather produced from materials such as plant fibers, mushrooms, and silicone can be influenced by the substrate, type, growth conditions, and post-treatment methods. For industrial applications, it is necessary to enhance physical strength, flexibility, and durability by using additional cross-linkers or plasticizers. Therefore, active research is being conducted to improve these physical characteristics for practical and commercial use.

Mycelium from mushrooms is composed of fibrous strands made up of a chitin-glucan complex, proteins, cellulose, or combinations thereof. The cross-linking of the mycelium primarily occurs through the amino groups of chitosan, which carries a distinctive positive charge, facilitating the bonding process.

For the cross-linking of chitosan via covalent bonding, agents such as EDC/NHS, glyoxal, glutaraldehyde, epichlorohydrin, diisocyanates, and genipin can be used.

For cross-linking methods utilizing non-covalent interactions, such as hydrogen bonding, electrostatic forces, and other hydrophobic interactions, agents like sodium sulfate, malic acid, tartaric acid, citric acid, and succinic acid can be employed.

Tannins are a type of plant-based polyphenol molecule abundant in nature, with over 800 different types identified. Among them, tannic acid (TA) is composed of a structure in which five galloyl groups are attached to a glucose core. Polyphenol molecules, such as galloyl groups, can form both covalent and non-covalent bonds with various other molecules, including hydrogen bonding, metal coordination bonding, pi-cation interactions, pi-pi stacking, nucleophilic addition reactions, and imine formation.

Additionally, tannic acid can bind with chitosan through hydrogen bonding, pi-cation interactions, imine formation, and nucleophilic addition reactions, and extensive research has been conducted on the binding of tannin-chitosan (TA-chitosan). However, most studies have been limited to fields such as films and adhesives, and no research has been reported on the leatherization of mycelium mats using tannic acid.

DISCLOSURE

Technical Problems

The objective of the present invention is to provide a leather material with enhanced physical strength, flexibility, and durability by utilizing mycelium, an eco-friendly material that can serve as a substitute for animal leather and petrochemical-based synthetic polymers.

Technical Solution

In order to achieve the aforementioned objective, the present invention provides a mycelium mat-based synthetic leather crosslinking composition containing tannic acid (TA), wherein the composition is characterized by enhanced crosslinking activity at a pH range of 7.5 to 9.5.

Additionally, the pH of the tannic acid composition may range from 8 to 9.5.

Additionally, the pH of the tannic acid composition may range from 8.5 to 9.5.

Additionally, the pH of the tannic acid composition may range from 8.5 to 9.1.

Furthermore, the present invention provides a method for manufacturing leather from a mycelium mat, comprising a first step of inactivating the mycelium mat; a second step of infiltrating the mycelium mat with a polysaccharide solution; a third step of infiltrating the polysaccharide-infused mycelium mat with a tannic acid solution; and a fourth step of infiltrating the tannic acid-infused mycelium mat with a buffering agent, wherein the pH of the tannic acid composition in the fourth step is between 7.5 and 9.5.

The tannic acid solution may include one or more solvents selected from ethanol at a concentration of 70-95% (v/v) and acetone at a concentration of 70-95% (v/v).

The buffering agent may be selected from one or more of the group consisting of hydrochloric acid (HCl), potassium hydroxide (KOH), sodium hydroxide (NaOH), sodium bicarbonate ($NaHCO_3$), bis-tris propane buffer, BES buffer (N,N-bis(2-hydroxyethyl)-2-aminoethanesulfonic acid), MOPS buffer (3-(N-morpholino) propanesulfonic acid), HEPES buffer (2-[4-(2-hydroxyethyl) piperazin-1-yl]ethanesulfonic acid), TES buffer (N-Tris(hydroxymethyl) methyl-2-aminoethanesulfonic acid), MOBS buffer (4-(N-morpholino)butanesulfonic acid), TRIS buffer (tris (hydroxymethyl)aminomethane), DIPSO buffer (3-(N,N-bis

[2-hydroxyethyl]amino)-2-hydroxypropanesulfonic acid), PBS buffer (phosphate-buffered saline), and glycine.

Additionally, the present invention provides a method for manufacturing leather from a mycelium mat, comprising the inclusion of one or more selected from the group consisting of chitosan, kappa-carrageenan (k-carrageenan), iota-carrageenan (i-carrageenan), lambda-carrageenan (l-carrageenan), guar gum, xanthan, gum arabic, pectin, peptone, konjac, dextran, heparin, fucoidan, and alginic acid.

Additionally, the present invention provides a method for manufacturing leather from a mycelium mat, further comprising a fifth step of plasticizing the crosslinked mycelium mat by treating it with a plasticizer solution.

Advantageous Effects

The leather material produced by the manufacturing method of the present invention is environmentally friendly due to the use of mycelium from mushrooms, and it is characterized by improved physical properties, such as tensile strength.

BEST MODE FOR INVENTION

Figure 1:
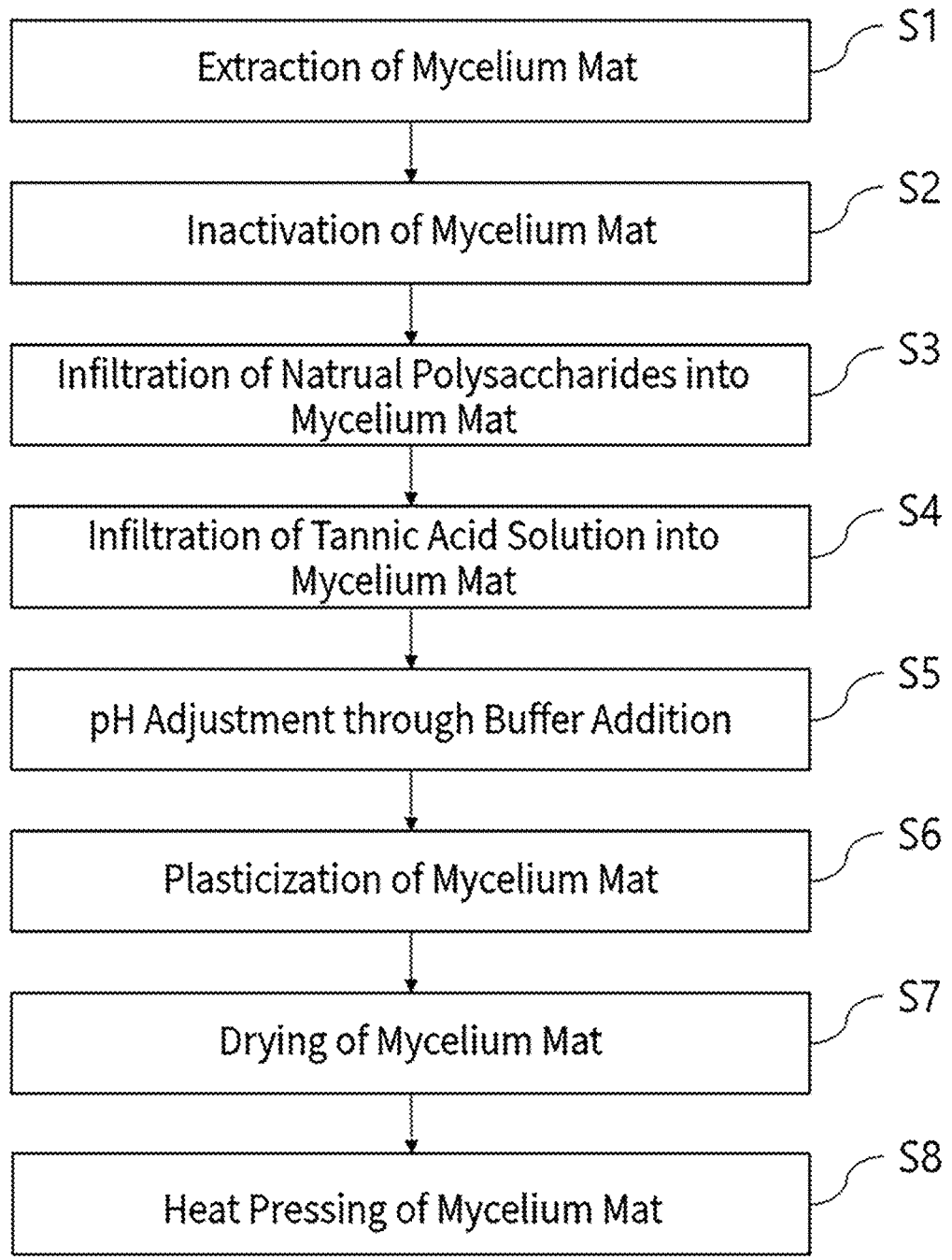
FIG. 1 is a schematic diagram illustrating the process of manufacturing leather using a mycelium mat according to one embodiment of the present invention.

The present invention will be described in detail through examples and experimental examples.

However, it should be understood that these examples and experimental examples are provided merely for illustrative purposes and are not intended to limit the scope of the invention to these specific embodiments.

Preparation Example: Extraction of Mycelium Mat

<Culture of Fungal Strains>

Potato dextrose agar (PDA) was dispensed into 90 mm petri dishes and allowed to solidify for 5 minutes, thereby preparing the PDA medium.

Under sterile conditions, a section of the mycelium from wood-decomposing mushrooms (*Ganoderma* sp., *Fomitella* sp., or *Inonotus* sp.) was cut and transferred onto the PDA medium. The culture was incubated at 28° C. for 7 days in an incubator.

Five mycelial sections, each measuring 10 mm$^2$, were excised from the strain cultured on PDA medium and inoculated into 500 mL of YPDB (potato dextrose broth containing 0.5% yeast extract) liquid medium. The inoculated medium was then agitated at 180 rpm and incubated at 25° C. for 7 days to culture the fungal strain.

<Liquid Culture>

At 25° C., 40 g of dextrose, 20 g of yeast extract, and 20 g of guar gum were mixed with 920 mL of distilled water to prepare the nutrient composition.

After preparing the nutrient composition, 0.5 g of magnesium sulfate ($MgSO_4$), 0.5 g of calcium carbonate ($CaCO_3$), 0.5 g of potassium phosphate ($KH_2PO_4$), and 0.5 g of calcium chloride ($CaCl_2$) were dissolved in 998 mL of distilled water at 25° C. to prepare the inorganic salt composition.

The nutrient composition and the inorganic salt composition were combined and mixed using a stirring device (DAIHAN Scientific, HT-120DX) at 25° C. and 200 rpm for 10 minutes to prepare a 2-liter medium composition.

The prepared medium composition was sterilized in an autoclave at 132° C. under a steam pressure of 5 kgf/cm$^2$ for 25 minutes. The sterilized medium was then cooled to 25° C. to create a semi-liquid medium, which was subsequently filled into half a vat (½ vat) up to 1000 mL.

In the original strain cultivation step, 200 mL of the composition containing the strain cultured at 25° C. for 7 days was inoculated into the 1000 mL of semi-liquid medium. The medium was then covered with a lid equipped with a filter and ventilation hole and incubated in the dark at 28° C. with 90% humidity for 4 weeks. After incubation, 300 g of living mycelium mat was extracted.

Example 1: Manufacture of Alternative Leather Using Mycelium Mat-pH 8.5 Condition The extracted mycelium mat from the preparation example was immersed in 400 mL of 30% hydrogen peroxide at 60° C. The mat was then subjected to ultrasonic treatment at a frequency of 35 kHz for 2 hours, while maintaining the temperature at 60° C.

At 25° C., 8 g of chitosan and 8 g of adipic acid were mixed with distilled water to prepare 400 mL of a 2% chitosan solution. The ultrasonically treated mycelium mat was then immersed in this chitosan solution and left at 25° C. for 1 day to ensure thorough absorption and treatment of the mat with the chitosan solution.

6.8 g of tannic acid was mixed with 400 mL of a 70% (v/v) ethanol aqueous solution at 25° C. to prepare an ethanolic tannic acid solution (10 mM, 400 mL).

Subsequently, the mycelium mat that had been immersed in the chitosan solution was transferred to the ethanolic tannic acid solution (10 mM, 400 mL) and soaked for 2 hours to ensure complete infiltration of the tannic acid into the mycelium mat.

After the 2-hour immersion treatment, the mycelium mat, which had been soaked in the ethanolic tannic acid solution, was transferred to a 10 mM tris buffer solution (pH 8.5, 400 mL) and immersed for 4 hours at 25° C.

60 mL of polyethylene glycol (PEG) was mixed with 340 mL of distilled water at 25° C. to prepare 400 mL of a 15% polyethylene glycol solution. The mycelium mat, which had been treated with the tannic acid solution, was then immersed in the prepared 15% polyethylene glycol solution (400 mL) and stirred at 200 rpm for 6 hours at 25° C.

The mycelium mat, which had been treated with the polyethylene glycol (PEG) solution, was dried at 40° C. for over 24 hours to remove moisture. After drying, the mat was subjected to hot pressing using a thermal press (Custom Village, CDH-4050) at 90° C. with a pressure of 98 MPa for 20 seconds. This process produced a mycelium leather sheet with dimensions of 27.5 cm in width, 21.5 cm in length, and 0.8 cm in thickness.

The manufactured mycelium leather was immersed in 100 mL of a primer solution composed of a polyurethane-based polymer and acetone (Hu Jeong Chemical, MR-100 Clear solution) at 25° C. for 1 hour. This treatment helps to improve the surface properties and adhesion characteristics of the mycelium leather.

The mycelium leather, which had been immersed in the primer solution, was then washed with an excess of 100% acetone solution for 10 minutes to remove any unreacted primer. After washing, the primer-free mycelium leather was dried at 60° C. for 5 minutes.

A coating solution was prepared by mixing an aqueous polyurethane dispersion (Hyu Jeong Chemical, PUD-A) with an aqueous colorant (Woo Shin Pigment, AQUA-LOR®) in a 9:1 ratio.

The dyed and dried mycelium leather was coated with the prepared coating solution at a rate of 120 cc/min, applied in five layers.

The mycelium leather, to which the coating solution had been applied, was dried at 100° C. for 5 minutes.

The dried mycelium leather was subjected to an embossing process using a press device equipped with an embossed pattern (DR-tech, model DR1003) heated to 110° C. The embossing was carried out by applying a pressure of 196 Pa for 20 seconds.

The embossed mycelium leather was laminated with a hot-melt adhesive film (JCC KOREA, F604L) measuring 27.5 cm in width, 21.5 cm in length, and 40 μm in thickness. A fiber reinforcement material (UMOFIL®) was placed over the adhesive film, and the layers were bonded using a thermal bonding device (Custom Village, CDH-4050) at 120° C. for 20 seconds. This process produced a mycelium leather product with final dimensions of 27.5 cm in width, 21.5 cm in length, and 0.12 cm in thickness.

The experimental procedure described above was repeated to prepare five mycelium leather samples, each measuring 27.5 cm in width, 21.5 cm in length, and 0.12 cm in thickness.

Example 2: Manufacture of Alternative Leather Using Mycelium Mat-pH 9 Condition

The step in Example 1, where the mycelium mat immersed in the ethanolic tannic acid solution was soaked in a pH 8.5 tris buffer solution (10 mM, 400 mL) at 25° C. for 4 hours after a 2-hour immersion, was directly replaced with a step in which the mycelium mat was soaked in a pH 9 tris buffer solution (10 mM, 400 mL) at 25° C. for 4 hours after the 2-hour immersion in the ethanolic tannic acid solution. All other steps were performed exactly the same, resulting in the preparation of five mycelium leather samples, each measuring 27.5 cm in width, 21.5 cm in length, and 0.12 cm in thickness.

Comparative Example 1: Manufacture of Alternative Leather Using Mycelium Mat-pH 5.7 Condition In Comparative Example 1, the step in Example 1 where the mycelium mat was soaked in a pH 8.5 tris buffer solution (10 mM, 400 mL) at 25° C. for 4 hours after the 2-hour immersion in the ethanolic tannic acid solution was omitted. Instead, the pH of the tannic acid solution was maintained at 5.7 throughout the process, while all other steps were performed identically. As a result, five mycelium leather samples, each measuring 25 cm in width, 20 cm in length, and 40 μm in thickness, were prepared.

Comparative Example 2: Manufacture of Alternative Leather Using Mycelium Mat-pH 7 Condition In Comparative Example 2, the step in Example 1 where the mycelium mat, after a 2-hour immersion in the ethanolic tannic acid solution, was soaked in a pH 8.5 tris buffer solution (10 mM, 400 mL) at 25° C. for 4 hours was replaced with a step where the mycelium mat was soaked in a pH 7 tris buffer solution (10 mM, 400 mL) at 25° C. for 4 hours following the 2-hour immersion in the ethanolic tannic acid solution. All other steps were carried out identically, resulting in the preparation of five mycelium leather samples, each measuring 27.5 cm in width, 21.5 cm in length, and 0.12 cm in thickness.

Comparative Example 3: Manufacture of Alternative Leather Using Mycelium Mat-pH 10 Condition In Comparative Example 3, the step in Example 1 where the mycelium mat, after a 2-hour immersion in the ethanolic tannic acid solution, was soaked in a pH 8.5 tris buffer solution (10 mM, 400 mL) at 25° C. for 4 hours was replaced with a step where the mycelium mat was soaked in a pH 10 tris buffer solution (10 mM, 400 mL) at 25° C. for 4 hours following the 2-hour immersion in the ethanolic tannic acid solution. All other processes were carried out in the same manner, resulting in the preparation of five mycelium leather samples, each measuring 27.5 cm in width, 21.5 cm in length, and 0.12 cm in thickness.

Experimental Example: Measurement of Tensile Strength

To confirm the improvement in tensile strength of the mycelium mat treated with the tannic acid solution and adjusted pH, the tensile strength of the mycelium leather samples prepared in Example 1, Example 2, Comparative Example 1, Comparative Example 2, and Comparative Example 3 was measured. The tensile strength tests were performed to evaluate the mechanical enhancement of the mycelium-based leather under different pH conditions.

Figure 2:
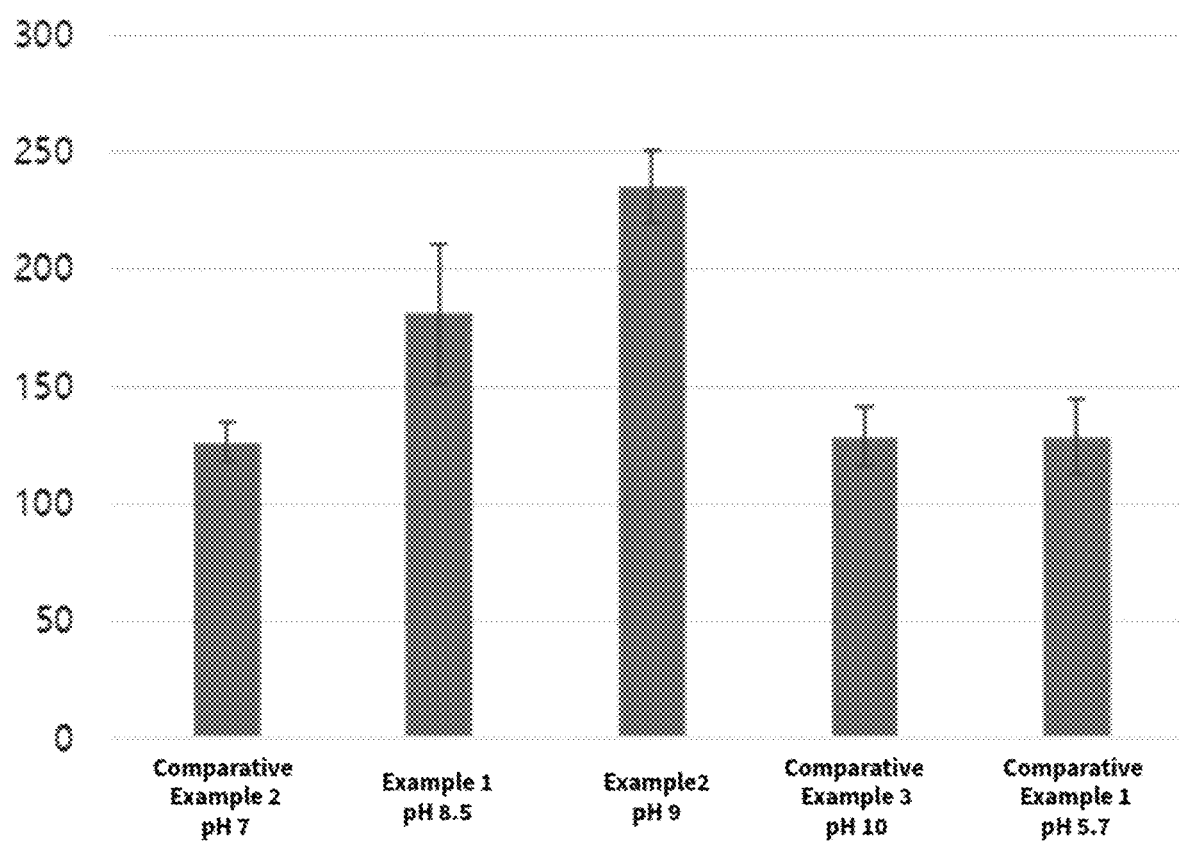
FIG. 2 is a graph showing the tensile strength measurement results of a leather sample manufactured using a mycelium mat according to one embodiment of the present invention.

The tensile strength was measured using a tensile tester (QMESYS). The mycelium leather samples from Example 1, Example 2, Comparative Example 1, Comparative Example 2, and Comparative Example 3 were clamped into the tensile tester and stretched at a rate of 100 mm/min until the leather samples fractured. The maximum tensile strength (N) at the point of fracture was recorded. The average tensile strength for five samples from each of Example 1, Example 2, Comparative Example 1, Comparative Example 2, and Comparative Example 3 was calculated. The results are shown in Table 1 and FIG. 2.

TABLE 1

| | Example 1 | Example 2 | Comparative Example 1 | Comparative Example 2 | Comparative Example 3 |
|---|---|---|---|---|---|
| tensile strength (N) | 181.43 | 235.47 | 128.67 | 126.36 | 128.67 |

S1: Extraction of Mycelium Mat
S2: Inactivation of Mycelium Mat
S3: Infiltration of Natural Polysaccharides into Mycelium Mat
S4: Infiltration of Tannic Acid Solution into Mycelium Mat
S5: pH Adjustment through Buffer Addition
S6: Plasticization of Mycelium Mat
S7: Drying of Mycelium Mat

Mode for Invention

Hereinafter, the present invention will be described in detail.

The present invention provides a crosslinking composition for synthetic leather based on a mycelium mat containing tannic acid (TA), wherein the composition is characterized by enhanced crosslinking activity at a pH range of 7.5 to 9.5.

As consumers' expectations for ethical consumption continue to rise, there is an increasing demand for alternative leathers (synthetic leathers) that do not involve extensive slaughter and environmental destruction in the process of obtaining leather.

However, the texture of synthetic leather differs significantly from that of natural leather, making the molding process more complex. Additionally, the increase in processing steps involving dyeing and adhesion has led to a sharp rise in manufacturing costs.

Furthermore, the use of petroleum-based polymers in manufacturing results in materials that are not easily biodegradable, making recycling impossible. This leads to significant environmental pollution throughout the entire production process, ultimately culminating in the disposal of industrial waste.

The inventors have developed the present invention, which involves a mycelium mat-based leather material that serves as an eco-friendly alternative to natural leather, such as animal hides, while also enhancing physical properties like tensile strength.

In the present invention, the term "tannic acid (TA)" is defined as a polyphenolic molecule characterized by a central glucose core and functionalized with five galloyl groups at the terminals. Its chemical formula is $C_{76}H_{52}O_{46}$, with a molecular weight of 1701.2 g/mol, and it has a CAS number of 1401-55-4.

Tannic acid, with its galloyl groups, can form both covalent and non-covalent bonds with various other molecules, including hydrogen bonding, metal coordination, pi-cation interactions, pi-pi stacking, nucleophilic addition reactions, and imine formation. Additionally, at pH levels near its pKa, tannic acid can modify the surfaces of various materials through oxidation, enabling secondary surface modifications as well.

In the present invention, the term "tannic acid composition" refers to a composition consisting of a tannic acid solution mixed with a buffering agent, which can be understood as equivalent to the synthetic crosslinking composition described in this specification. By adjusting the pH of the tannic acid composition, the activity of the crosslinking reaction of the mycelium mat can be enhanced.

The pH of the tannic acid composition may range from 7.5 to 9.5, preferably from 8 to 9.5, more preferably from 8.5 to 9.5, and most preferably from 8.5 to 9.1. This pH can be adjusted through the action of basic solvents or buffering agents such as hydrochloric acid (HCl), potassium hydroxide (KOH), sodium hydroxide (NaOH), sodium bicarbonate ($NaHCO_3$), bis-tris propane buffer, BES buffer (N,N-bis(2-hydroxyethyl)-2-aminoethanesulfonic acid), MOPS buffer (3-(N-morpholino)propanesulfonic acid), HEPES buffer (2-[4-(2-hydroxyethyl)piperazin-1-yl]ethanesulfonic acid), TES buffer (N-Tris(hydroxymethyl)methyl-2-aminoethanesulfonic acid), MOBS buffer (4-(N-Morpholino)butanesulfonic acid), TRIS buffer (tris(hydroxymethyl)aminomethane), DIPSO buffer (3-(N,N-Bis[2-hydroxyethyl]amino)-2-hydroxypropanesulfonic acid), phosphate-buffered saline (PBS), and glycine.

The galloyl groups of the tannic acid can undergo oxidation under slightly basic conditions to form quinones. The oxidized quinones can react with nucleophilic functional groups (such as amino and thiol groups) present in chitosan and the mycelium mat, leading to nucleophilic addition reactions or forming imine bonds through dehydration condensation, resulting in covalent bonding.

The pH of the tannic acid composition may range from 7.5 to 9.5, preferably from 8 to 9.5, more preferably from 8.5 to 9.5, and most preferably from 8.5 to 9.1. If the pH is below 7.5, the formation of semiquinones through the oxidation of galloyl groups in tannic acid may be reduced, resulting in insufficient activation of the crosslinking reaction of the mycelium. Conversely, if the pH exceeds 9.5, the semiquinone form may not be maintained, leading to over-oxidation to quinones or hydrolysis of the tannic acid, which can prevent the crosslinking reaction from occurring.

By optimizing the pH of the tannic acid composition to the range of 7.5 to 9.5, it was confirmed that the tensile strength of the mycelium mat significantly improved when manufactured into leather (Experimental Example).

The present invention provides a crosslinking composition for synthetic leather based on a mycelium mat, wherein the tannic acid is present at a concentration of 1 to 20 mM relative to the total volume of the tannic acid solution.

The present invention provides a method for manufacturing leather from a mycelium mat, comprising: a first step of inactivating the mycelium mat; a second step of allowing a polysaccharide solution to infiltrate the mycelium mat; a third step of allowing a tannic acid solution to penetrate the mycelium mat that has been treated with the polysaccharide solution; and a fourth step of allowing a buffering agent to infiltrate the mycelium mat that has been treated with the tannic acid solution, wherein the pH of the tannic acid composition in the fourth step may range from 7.5 to 9.5.

In the present invention, the term "inactivation of the mycelium mat" refers to the reduction or inhibition of the biological activity of the mycelium.

In the present invention, the mycelium mat is cultivated using mycelial segments isolated from wood-decomposing mushrooms, such as *Ganoderma* sp., *Fomitella* sp., or *Inonotus* sp. Specifically, mycelial segments isolated from *Inonotus obliquus* (chaga mushroom), *Phellinus linteus* (sanghwang mushroom), or *Ganoderma lucidum* (reishi mushroom) may be used; however, this is not limited to these species. The cultivation of the mycelium may employ known methods using solid or semi-liquid media.

In the present invention, the first step of inactivating the mycelium mat may be included, wherein methods such as sterilization, ultrasonic treatment, or chemical treatment may be employed.

The sterilization method may involve the use of an autoclave, wherein the living mycelium is sterilized under conditions of temperature and pressure that exceed the maximum limits for living organisms, specifically at 119° C. and 1.2 atm. More specifically, the mycelium mat can be inactivated by sterilizing it at 121° C. and 1.5 atm for 30 minutes.

The inactivation of the mycelium mat using ultrasonic treatment may be conducted by immersing the living mycelium in distilled water within a frequency range of 35 to 50 kHz for a duration of 2 hours.

The chemical treatment method may involve the use of hydrogen peroxide ($H_2O_2$), sodium hypochlorite (NaClO), or sodium hydroxide (NaOH) to inactivate the mycelium mat.

The hydrogen peroxide solution reacts with enzymes to generate reactive oxygen species or oxygen radicals, which can degrade cell walls or cell membranes. A 3% hydrogen peroxide solution is commonly used for medical purposes.

In the treatment method utilizing hydrogen peroxide solution in the present invention, the concentration of hydrogen peroxide may range from 5% to 30% relative to the total volume of the solution. The mycelium mat can be immersed in this solution at temperatures between 25° C. and 60° C. for a duration of 1 minute to 2 hours. If the concentration of hydrogen peroxide is between 10% and 30%, ultrasonic treatment should be performed for more than 1 hour prior to the hydrogen peroxide solution treatment.

Sodium hypochlorite is known as the main component of bleach and can be diluted for use in disinfection purposes depending on the application.

In the treatment method using sodium hypochlorite solution in the present invention, the concentration of sodium hypochlorite may range from 0% to 30% relative to the total volume of the solution. The mycelium mat can be immersed in this solution at temperatures between 25° C. and 60° C. for a duration of 1 minute to 2 hours. To effectively inactivate the mycelium, it is preferable to use a solution containing at least 5% sodium hypochlorite and perform ultrasonic treatment for more than 1 hour during immersion, or to immerse the mycelium mat in a solution of 5% or more sodium hypochlorite for at least 2 hours without ultrasonic treatment.

In the present invention, the second step involves allowing a polysaccharide solution to infiltrate the mycelium mat, wherein the polysaccharide included in the solution may be selected from the group consisting of chitosan, kappa-carrageenan (k-carrageenan), iota-carrageenan (I-carrageenan), lambda-carrageenan (L-carrageenan), guar gum, xanthan, gum arabic, pectin, peptone, konjac, dextran, heparin, fucoidan, and alginic acid.

In the present invention, chitosan and adipic acid can be infiltrated into the inactivated mycelium mat. However, simply infiltrating chitosan and adipic acid followed by low-temperature drying and then heat pressing may be unsuitable for crosslinking through amide bonds that can form between the amine groups of chitosan and the carboxyl groups of adipic acid.

Therefore, the present invention includes a third step of allowing a tannic acid solution to penetrate the mycelium mat that has been treated with the polysaccharide solution.

The galloyl groups of tannic acid can undergo oxidation under slightly basic conditions to form quinones. The oxidized quinones can react with nucleophilic functional groups (such as amino and thiol groups) present in chitosan and the mycelium mat, leading to nucleophilic addition reactions or forming imine bonds through dehydration condensation, resulting in covalent bonding.

The present invention may include a fourth step in which a buffering agent is allowed to infiltrate the mycelium mat that has been treated with the tannic acid solution. In this fourth step, the tannic acid solution may be mixed with the buffering agent to form a tannic acid composition.

The pH of the tannic acid composition may range from 7.5 to 9.4, 7.5 to 9.3, 7.5 to 9.2, 7.5 to 9.1, 7.5 to 9.0, 7.5 to 8.9, 7.5 to 8.8, 7.5 to 8.7, 7.5 to 8.6, 7.5 to 8.5, 7.5 to 8.4, 7.5 to 8.3, 7.5 to 8.2, 7.5 to 8.1, 7.5 to 8.0, 7.5 to 7.9, 7.5 to 7.8, 7.5 to 7.7, 7.5 to 7.6, 7.6 to 9.4, 7.6 to 9.3, 7.6 to 9.2, 7.6 to 9.1, 7.6 to 9.0, 7.6 to 8.9, 7.6 to 8.8, 7.6 to 8.7, 7.6 to 8.6, 7.6 to 8.5, 7.6 to 8.4, 7.6 to 8.3, 7.6 to 8.2, 7.6 to 8.1, 7.6 to 8.0, 7.6 to 7.9, 7.6 to 7.8, 7.6 to 7.7, 7.7 to 9.4, 7.7 to 9.3, 7.7 to 9.2, 7.7 to 9.1, 7.7 to 9.0, 7.7 to 8.9, 7.7 to 8.8, 7.7 to 8.7, 7.7 to 8.6, 7.7 to 8.5, 7.7 to 8.4, 7.7 to 8.3, 7.7 to 8.2, 7.7 to 8.1, 7.7 to 8.0, 7.7 to 7.9, 7.7 to 7.8, 7.8 to 9.4, 7.8 to 9.3, 7.8 to 9.2, 7.8 to 9.1, 7.8 to 9.0, 7.8 to 8.9, 7.8 to 8.8, 7.8 to 8.7, 7.8 to 8.6, 7.8 to 8.5, 7.8 to 8.4, 7.8 to 8.3, 7.8 to 8.2, 7.8 to 8.1, 7.8 to 8.0, 7.8 to 7.9, 7.9 to 9.4, 7.9 to 9.3, 7.9 to 9.2, 7.9 to 9.1, 7.9 to 9.0, 7.9 to 8.9, 7.9 to 8.8, 7.9 to 8.7, 7.9 to 8.6, 7.9 to 8.5, 7.9 to 8.4, 7.9 to 8.3, 7.9 to 8.2, 7.9 to 8.1, 7.9 to 8.0, 8.0 to 9.4, 8.0 to 9.3, 8.0 to 9.2, 8.0 to 9.1, 8.0 to 9.0, 8.0 to 8.9, 8.0 to 8.8, 8.0 to 8.7, 8.0 to 8.6, 8.0 to 8.5, 8.0 to 8.4, 8.0 to 8.3, 8.0 to 8.2, 8.0 to 8.1, 8.1 to 9.4, 8.1 to 9.3, 8.1 to 9.2, 8.1 to 9.1, 8.1 to 9.0, 8.1 to 8.9, 8.1 to 8.8, 8.1 to 8.7, 8.1 to 8.6, 8.1 to 8.5, 8.1 to 8.4, 8.1 to 8.3, 8.1 to 8.2, 8.2 to 9.4, 8.2 to 9.3, 8.2 to 9.2, 8.2 to 9.1, 8.2 to 9.0, 8.2 to 8.9, 8.2 to 8.8, 8.2 to 8.7, 8.2 to 8.6, 8.2 to 8.5, 8.2 to 8.4, 8.2 to 8.3, 8.3 to 9.4, 8.3 to 9.3, 8.3 to 9.2, 8.3 to 9.1, 8.3 to 9.0, 8.3 to 8.9, 8.3 to 8.8, 8.3 to 8.7, 8.3 to 8.6, 8.3 to 8.5, 8.3 to 8.4, 8.4 to 9.4, 8.4 to 9.3, 8.4 to 9.2, 8.4 to 9.1, 8.4 to 9.0, 8.4 to 8.9, 8.4 to 8.8, 8.4 to 8.7, 8.4 to 8.6, 8.4 to 8.5, 8.5 to 9.4, 8.5 to 9.3, 8.5 to 9.2, 8.5 to 9.1, 8.5 to 9.0, 8.5 to 8.9, 8.5 to 8.8, 8.5 to 8.7, 8.5 to 8.6, 8.6 to 9.4, 8.6 to 9.3, 8.6 to 9.2, 8.6 to 9.1, 8.6 to 9.0, 8.6 to 8.9, 8.6 to 8.8, 8.6 to 8.7, 8.7 to 9.4, 8.7 to 9.3, 8.7 to 9.2, 8.7 to 9.1, 8.7 to 9.0, 8.7 to 8.9, 8.7 to 8.8, 8.8 to 9.4, 8.8 to 9.3, 8.8 to 9.2, 8.8 to 9.1, 8.8 to 9.0, 8.8 to 8.9, 8.9 to 9.4, 8.9 to 9.3, 8.9 to 9.2, 8.9 to 9.1, 8.9 to 9.0, 9.0 to 9.4, 9.0 to 9.3, 9.0 to 9.2, 9.0 to 9.1, etc.

By adjusting the pH of the tannic acid composition within the range of 7.5 to 9.5 to optimize the activity of the crosslinking reaction, it has been confirmed that the tensile strength of the mycelium mat significantly improves when manufactured into leather within this pH range (Examples 1 and 2, Experimental Example). The tannic acid solution comprises one or more solvents selected from the group consisting of ethanol at a concentration of 70-95% (v/v) and acetone at a concentration of 70-95% (v/v).

The ethanol or acetone included in the tannic acid solution can dissolve tannic acid; however, the polysaccharides contained in the polysaccharide solution, which will be described later, cannot be dissolved. Therefore, when the mycelium mat, which is infiltrated with chitosan, is immersed in a tannic acid solution dissolved in ethanol, only the tannic acid can penetrate into the mycelium mat. This results in the maximization of crosslinking bonds, enhancing the overall properties of the material.

The concentration of ethanol or acetone included in the tannic acid solution may range from 70% to 95% (v/v). If the concentration is below 70%, there may be issues where the polysaccharides that have previously infiltrated the mycelium dissolve and leach out, or the tannic acid may react before entering the mycelium mat, resulting in a loss of activity. Conversely, if the concentration exceeds 95%, the solubility of tannic acid may not be achieved.

The solvents included in the tannic acid solution may refer to a 70% to 95% (v/v) ethanol aqueous solution, a 70% to 95% (v/v) acetone aqueous solution, or a mixture thereof. Additionally, other solvents that can dissolve powdered tannic acid to enhance its activity may also be utilized in the tannic acid solution.

The buffering agent may be one or more selected from the group consisting of hydrochloric acid (HCl), potassium hydroxide (KOH), sodium hydroxide (NaOH), sodium bicarbonate ($NaHCO_3$), bis-tris propane buffer, BES buffer (N,N-bis(2-hydroxyethyl)-2-aminoethanesulfonic acid), MOPS buffer (3-(N-morpholino)propanesulfonic acid), HEPES buffer (2-[4-(2-hydroxyethyl)piperazin-1-yl]ethanesulfonic acid), TES buffer (N-Tris(hydroxymethyl)methyl-2-aminoethanesulfonic acid), MOBS buffer (4-(N-Morpholino)butanesulfonic acid), TRIS buffer (tris (hydroxymethyl)aminomethane), DIPSO buffer (3-(N,N-bis[2-hydroxyethyl]amino)-2-hydroxypropanesulfonic acid), phosphate-buffered saline (PBS), and glycine.

The buffering agent adjusts the pH of the tannic acid composition to a slightly basic level, enabling the oxidation of the galloyl groups in tannic acid to form quinones. The oxidized quinones can react with the nucleophilic functional groups (such as amino and thiol groups) present in chitosan and the mycelium mat, resulting in nucleophilic addition reactions or the formation of imine bonds through dehydration condensation, thereby facilitating covalent bonding.

Specifically, the pH of the tannic acid composition may range from 7.5 to 9.5. If the pH is below 7.5, the formation of semiquinones through the oxidation of the galloyl groups in tannic acid may be reduced, leading to insufficient crosslinking of the mycelium. Conversely, if the pH exceeds 9.5, the semiquinone form may not be maintained, resulting in over-oxidation to quinones or hydrolysis of the tannic acid, which can prevent the crosslinking reaction from occurring.

By adjusting the pH of the tannic acid composition within the range of 7.5 to 9.5 to optimize the crosslinking reaction, it was confirmed that the tensile strength of the mycelium mat significantly improved when manufactured into leather within this pH range (Experimental Example).

The present invention may include a step of adding a crosslinking agent to enhance the crosslinking reaction of the mycelium mat, which can be incorporated into the processes before and after the fourth step, where the pH of the tannic acid composition formed by the introduction of the buffering agent is adjusted to the range of 7.5 to 9.5.

The crosslinking agents that may be included in this step can be one or more selected from the group consisting of N-ethylcarbodiimide hydrochloride (EDC), EDC/NHS, carbodiimidazole, N,N'-dicyclohexylcarbodiimide, disuccinimidyl carbonate, disuccinimidyl suberate, glyoxal, glutaraldehyde, epichlorohydrin, genipin, or one or more isocyanates, isothiocyanates, acrylamides, NHS esters, sulfonyl chlorides, aldehydes, imidoesters, diazoalkanes, diazoacetyls, epoxides, and alkyl halides, which are characterized by having functional groups.

Additionally, the present invention provides a method for manufacturing leather from a mycelium mat that further includes a fifth step of plasticizing the crosslinked mycelium mat with a plasticizer solution.

In this invention, the term "plasticize" refers to the use of an additive that reduces the viscosity or brittleness of a material. It signifies a substance added to alter the physical properties of a polymer, such as its softening point, glass transition temperature, and thermal and mechanical properties. The plasticizer may be a material commonly used in the production of plastics.

The plasticizer solution may comprise one or more components selected from the group consisting of ethylene glycol, ethylene glycerol, glycerol, polyethylene glycol (PEG), polypropylene glycol (PPG), polysorbate, cyclodextrin, lavender oil, castor oil, and cinnamaldehyde.

In a specific embodiment of the present invention, a crosslinking composition for synthetic leather containing pH-adjusted tannic acid was used to produce mycelium mat-based leather samples, and the tensile strength of the manufactured leather was measured (Experimental Example).

INDUSTRIAL APPLICABILITY

The present invention relates to a crosslinking composition for synthetic leather based on a mycelium mat containing tannic acid (TA) and a method for producing leather from this mycelium mat. The mycelium mat produced by the method utilizes mycelium from mushrooms, an eco-friendly material, to serve as an alternative to animal leather and petrochemical-based synthetic polymers. The resulting leather material offers enhanced physical strength, flexibility, and durability, making it suitable for various industrial applications and highlighting its commercial viability.

The invention claimed is:

1. A method for producing leather from a mycelium mat, comprising:
    a first step of inactivating the mycelium mat;
    a second step of allowing a polysaccharide solution to infiltrate the mycelium mat;
    a third step of allowing a tannic acid solution to infiltrate the mycelium mat that has been treated with the polysaccharide solution; and
    a fourth step of allowing a buffering agent to infiltrate the mycelium mat that has been treated with the tannic acid solution,
    wherein a tannic acid composition, formed by infiltration of the buffering agent into the mycelium mat treated with the tannic acid solution, has a pH between 8.3 and 9.2.

2. The method of claim 1,
    wherein the polysaccharide solution comprises one or more components selected from the group consisting of chitosan, kappa-carrageenan (k-carrageenan), iota-carrageenan (I-carrageenan), lambda-carrageenan (L-carrageenan), guar gum, xanthan, gum arabic, pectin, peptone, konjac, dextran, heparin, and fucoidan.

3. The method of claim 1,
    wherein the tannic acid solution comprises one or more solvents selected from the group consisting of ethanol at a concentration of 70-95% v/v and acetone at a concentration of 70-95% v/v.

4. The method of claim 3,
    wherein the buffering agent is one or more selected from the group consisting of hydrochloric acid (HCl), potassium hydroxide (KOH), sodium hydroxide (NaOH), sodium bicarbonate ($NaHCO_3$), bis-tris propane buffer, BES buffer (N,N-bis(2-hydroxyethyl)-2-aminoethanesulfonic acid), MOPS buffer (3-(N-morpholino) propanesulfonic acid), HEPES buffer (2-[4-(2-hydroxyethyl) piperazin-1-yl]ethanesulfonic acid), TES buffer (N-Tris(hydroxymethyl)methyl-2-aminoethanesulfonic acid), MOBS buffer (4-(N-Morpholino) butanesulfonic acid), TRIS buffer (tris(hydroxymethyl)aminomethane), DIPSO buffer (3-(N,N-Bis[2-hydroxyethyl]amino)-2-hydroxypropanesulfonic acid), phosphate-buffered saline (PBS), and glycine.

5. The method of claim 1,
    further comprising a fifth step of plasticizing the mycelium mat with a plasticizer solution after the fourth step.

6. The method of claim 5,
    wherein the plasticizer solution comprises one or more components selected from the group consisting of ethylene glycol, ethylene glycerol, glycerol, polyethylene glycol (PEG), polypropylene glycol (PPG), polysorbate, cyclodextrin, lavender oil, castor oil, and cinnamaldehyde.

\* \* \* \* \*